United States Patent [19]

Magami et al.

[11] Patent Number: 4,695,649

[45] Date of Patent: Sep. 22, 1987

[54] PHTHALATE COMPOUNDS

[75] Inventors: Masato Magami; Kazumi Saeki, both of Nakatsu; Takanori Miura, Chikujo; Takeshi Inoue, Nakatsu, all of Japan

[73] Assignee: Yoshitomi Pharmaceutical Industries, Ltd., Osaka, Japan

[21] Appl. No.: 748,450

[22] PCT Filed: Apr. 16, 1985

[86] PCT No.: PCT/JP85/00208

§ 371 Date: Jun. 12, 1985

§ 102(e) Date: Jun. 12, 1985

[87] PCT Pub. No.: WO85/04869

PCT Pub. Date: Nov. 7, 1985

[30] Foreign Application Priority Data

Apr. 19, 1984 [JP] Japan .................................. 59-78907

[51] Int. Cl.$^4$ ................................................ C07C 69/80
[52] U.S. Cl. ........................................ 560/86; 560/85; 562/480
[58] Field of Search .................... 560/85, 86; 562/480

[56] References Cited

U.S. PATENT DOCUMENTS 1,912,734  6/1933  Stand et al. .......................... 560/86
3,966,685  6/1976  Allard .................................. 528/66
4,440,945  4/1984  Conciatori et al. ................... 560/86

FOREIGN PATENT DOCUMENTS 400970  of 1924  Fed. Rep. of Germany ........ 560/86
49-067993  7/1974  Japan .................................... 560/86

OTHER PUBLICATIONS

Chemical Abstracts, Tenth Collective Index, Formulas, p. 14802F, entry C$_{24}$H$_{18}$O$_8$, (1983).

Primary Examiner—Werren B. Lone
Assistant Examiner—Vera C. Clarke
Attorney, Agent, or Firm—Wenderoth, Lind & Ponack

[57] ABSTRACT

A phthalate compound represented by the formula:

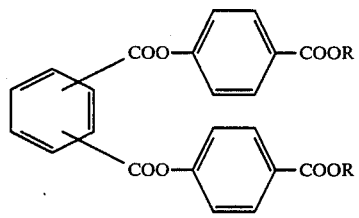

wherein R is alkyl having 1-8 carbon atoms or benzyl. The compounds have a repellency action to unhygienic pests and a plasticization action to thermoplastic polymers, and are useful as a pesticide or plasticizer.

1 Claim, No Drawings

PHTHALATE COMPOUNDS

TECHNICAL FIELD AND DISCLOSURE OF THE INVENTION

This invention relates to novel phthalates represented by the general formula:

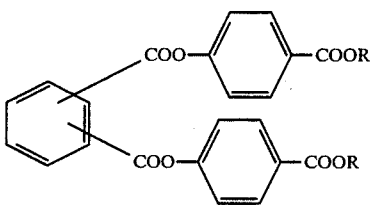

wherein R is alkyl having 1-8 carbon atoms, e.g., methyl, ethyl, propyl, isopropyl, butyl, isobutyl, sec-butyl, tert-butyl, pentyl, neopentyl, hexyl, heptyl, octyl, tert-octyl, etc. or benzyl.

The compounds of formula (I) can be readily prepared by making to react a compound of the formula:

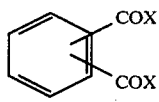

wherein X is halogen, e.g., chlorine or bromine, with a compound of the formula:

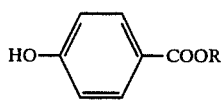

wherein R is the same as defined above, in a suitable solvent such as toluene, benzene, xylene, etc. in the presence of an amine such as triethylamine, pyridine, dimethylaniline, etc.

The resulting product is purified by a conventional method such as column chromatography, recrystallization.

The compounds of this invention have a repellency action against unhygienic pests, e.g., cockroaches, termites, etc. and accordingly, are useful as a pest-repellent.

In using the compound of this invention as a pest-repellent, it is mixed with a conventional carrier for a pest-repellent, kneaded in a synthetic resin, e.g., polyvinyl chloride or any other material intended for repellency of unhygienic pests, coated or impregnated with a brush or by spraying.

The amount in which the compound is used varies depending on the mode of use and is such that is enough to exhibit a repellency action to unhygienic pests. For example, 0.5 to 10 parts by weight of it may be compounded to 1 part by weight of a carrier.

Further, the compounds of this invention impart a superior plasticization efficiency to a thermoplastic polymer and increase its suppleness, elasticity, plasticity with a low volatility. Hence, they are also useful as a plasticizer for polymers.

Particularly, they are suitable as a plasticizer for nylon resins (nylon 6, nylon 66, etc.). For instance, it is preferred that the compound of this invention is added in an amount of 0.5 to 5% by weight, preferably 1 to 4% by weight to nylon chips, and the mixture is preheated to 70°-80° C. for a few hours and subjected to molding treatment according to conventional method.

It is a further feature that the compounds of this invention, when incorporated in a nylon resin, lower the softening temperature of it. As a consequence, it is possible to lower the processing temperature of it and to perform stable processing because of a low thermal volatility.

The invention will be hereinbelow described in detail with reference to examples and experimental examples.

EXAMPLE 1

Into a 500 ml four-neck flask equipped with a condenser tube and a thermometer are charged 56 g of benzyl p-hydroxybenzoate, 25 g of triethylamine and 60 ml of toluene. A suspension of 25 g of terephthalic dichloride in 100 ml of toluene is added dropwise with stirring while retaining the mixture at 0°-5° C. over 3 hours. After addition, the mixture is further allowed to react at 0°-5° C. for 1 hour. Thereafter the resulting reaction product is collected by filtration to obtain white crystals. The crystals are washed with 1500 ml of water twice and then with 1000 ml of methanol twice and subsequently, recrystallized from chloroform to give di(p-benzyloxycarbonylphenyl)terephthalate melting at 186°-187° C. as white crystals.

EXAMPLE 2

Into a 500 ml four-neck flask equipped with a condenser tube and a thermometer are charged 56 g of benzyl p-hydroxybenzoate, 25 g of triethylamine and 160 ml of toluene. A suspension of 25 g of isophthalic dichloride in 100 ml of toluene is added dropwise with stirring while maintaining the mixture at 0°-3° C. over 3 hours. After addition, the mixture is further allowed to react at 0°-3° C. for 1 hour. Thereafter, the resulting reaction product is collected by filtration to obtain white crystals. The crystalline product is washed with 1500 ml of water twice and then with 1000 ml of methanol twice and subsequently, recrystallized from a mixture solvent of hexane-chloroform (1:1) to give di(p-benzyloxycarbonylphenyl)isophthalate melting at 105°-107° C. as white crystals.

EXAMPLE 3

Into a 500 ml four-neck flask equipped with a condenser tube and a thermometer are charged 56 g of benzyl p-hydroxybenzoate, 25 g of triethylamine and 160 ml of toluene. A solution of 25 g of phthalic dichloride in 100 ml of toluene is added dropwise with stirring while maintaining the mixture at 0°-3° C. over 3 hours. After addition, the mixture is further allowed to react at 0°-3° C. for 1 hour. Then the reaction product is filtered, the filtrate solution is washed with 500 ml of water twice and concentrated under diminished pressure to distill the toluene off, and thereafter, 100 ml of hexane is added to the solution with stirring to give white crystals. The product is recrystallized from a mixture solvent of hexane-ethyl acetate (1:1) to yield di(p-benzyloxycarbonylphenyl)phthalate melting at 100°-103° C. as white crystals.

EXAMPLE 4

Into a 500 ml four-neck flask equipped with a condenser tube and a thermometer are charged 20 g of p-hydroxybenzoate, 13.1 g of triethylamine and 100 ml of toluene. A solution of 13.2 g of phthalic dichloride in 40 ml of toluene is added dropwise with stirring while maintaining the mixture at 0°–5° C. over 1 hour. After addition, the mixture is further allowed to react at 0°–5° C. for one hour. The resulting reaction product is washed with 1000 ml of water three times and concentrated under diminished pressure to distill the toluene off. The residue is recrystallized from toluene to yield di(p-methoxycarbonylphenyl)phthalate, m.p. 123°–125° C., as white crystals.

EXAMPLE 5

Into a 1000 ml four-neck flask equipped with a condenser tube and a thermometer ae charged 20 g of methyl p-hydroxybenzoate, 13.1 g of triethylamine and 100 ml of toluene. A suspension of 13.2 g of isophthalic dichloride in 110 ml of toluene is added dropwise with stirring over one hour while maintaining the mixture at 0°–5° C. After finishing of addition, 500 ml of methanol is added and the resulting mixture is further stirred for 30 minutes. The reaction product is collected by filtration as white crystals. The product is washed with 1000 ml of water two times and 500 ml of methanol once and recrystallized from a mixture solvent of ethyl acetate-chloroform (1:1) to yield di(p-methoxycarbonylphenyl)isophthalate, m.p. 215°–217° C., as white crystals.

EXAMPLE 6

The procedure of Example 5 is repeated except that terephtahlic dichloride is used instead of isophthalic dichloride. The reaction product is recrystallized from chloroform to yield di(p-methoxycarbonylphenyl)-terephthalate, m.p. 243°–245° C., as white crystals.

EXAMPLE 7

A similar procedure to Example 5 is carried out by using ethyl p-hydroxybenzoate and isophthalic dichloride. The reaction product is recrystallized from chloroform-ethyl acetate (1:1) to yield di(p-ethoxycarbonylphenyl)isophthalate, m.p. 123°–125° C., as white crystals.

EXAMPLE 8

The procedure of Example 5 is conducted except that ethyl p-hydroxybenzoate and terephthalic dichloride are substituted. The reaction product is recrystallized from ethyl acetate-chloroform (1:1) to yield di(p-ethoxycarbonylphenyl)terephthalate, m.p. 187°–189° C., as white crystals.

EXAMPLE 9

Propyl p-hydroxybenzoate and phthalic dichloride are allowed to react and treated in a similar procedure to Example 4. The residue obtained is recrystallized from hexane and recrystallized from ethyl acetate-chloroform (1:1) to yield di(p-propoxycarbonylphenyl)phthalate, m.p. 87°–89° C., as white crystals.

EXAMPLE 10

Propyl p-hydroxybenzoate and terephthalic dichloride are allowed to react in a similar procedure to Example 5. The reaction product is recrystallized from hexane-chloroform (1:1) to yield di(p-propoxycarbonylphenyl)terephthalate, m.p. 136°–139° C., as white crystals.

EXAMPLE 11

Butyl p-hydroxybenzoate and terephthalic dichloride are allowed to react in a similar procedure to Example 5. The product is recrystallized from hexane-chloroform (1:1) to give di(p-butoxycarbonylphenyl)-terephthalate, m.p. 128°–131° C., as white crystals.

EXAMPLE 12

Octyl p-hydroxybenzoate and terephthalic dichloride are allowed to react and treated in a similar procedure to Example 4. The residue obtained is recrystallized from ethyl acetate-chloroform (1:1) to give di(p-octyloxycarbonylphenyl)terephthalate, m.p. 108°–110° C., as white crystals.

EXAMPLE 13

Octyl p-hydroxybenzoate and isophthalic dichloride are made to react and treated in a similar procedure to Example 4 to yield di(p-octyloxycarbonylphenyl)isophthalate in a pale yellow oily state.

EXPERIMENTAL EXAMPLE 1

The compounds of this invention are each dissolved in methanol to prepare a 10,000 ppm solution. A square filter paper of 12×9 cm in size is impregnated with 1 ml of the solution, dried in air, and then attached to a veneer shelter having a size of 12×9 cm and a height of 1 cm on its inner bottom. Non-treated filter paper is similarly attached to another shelter. Both shelters are placed in a plastic container and 200 German cockroaches are released in it. After the container is allowed to stand overnight, number of them dwelling in each of the shelters is counted, and repellency rate (%) is calculated. The results are shown in Table 1 below.

$$\text{Repellency rate (\%)} = \frac{\left(\begin{array}{c}\text{Number in non-}\\\text{treated shelter}\end{array}\right) - \left(\begin{array}{c}\text{Number in treated}\\\text{shelter}\end{array}\right)}{(\text{Number in non-treated shelter})} \times 100$$

TABLE 1

| Compound | Repellency Rate (%) | | | |
|---|---|---|---|---|
| | 1 | 2 | 3 | Average |
| Compound of Example 3 | 95.2 | 89.6 | 92.5 | 92.4 |
| Compound of Example 9 | 90.4 | 94.4 | 95.0 | 93.3 |
| Compound of Example 13 | 88.8 | 98.2 | 92.2 | 93.1 |

EXPERIMENTAL EXAMPLE 2

The compound of Example 13 is compounded in nylon 6 chips as shown in Table 2. The mixtures are each preheated at 70°–80° C. for 5–6 hours, injection-molded at 250° C. and measured by the method according to JIS K 6871 with respect to thermal deformation temperature. The results obtained are shown in Table 2.

TABLE 2

| | 1 | 2 | 3 | 4 | 5 |
|---|---|---|---|---|---|
| Compounding Concentration of Compound (%) | 0 | 0.5 | 1 | 4 | 5 |
| Thermal Deformation Temperature (°C.) | 47 | 49 | 51 | 52 | 52 |

EXPERIMENTAL EXAMPLE 3

Compound of Example 13 and a control compound of octyl p-oxybenzoate are tested by recording curves of weight decrease due to temperature rise of them at an elevating temperature speed of 5° C./min at a chart speed of 10 mm/min in the atmosphere of nitrogen gas with a thermobalance measuring device TSG-1. From the weight decrease curves obtained, volatilization due to heat and decomposition process of the compounds can be known. The temperature at which the weight decrease reaches 50% is measured. As a result, the 50% decrease temperature of Compound of Example 13 is 394° C., whereas that of the control compound is 254° C.

The invention has been fully described in the foregoing description and examples included therein, but they may be altered or modified in various ways without departing from the spirit and scope of this invention.

We claim:

1. Di(p-benzyloxycarbonylphenyl)isophthalate.

* * * * *